United States Patent [19]

Hirsch

[11] 4,358,015
[45] Nov. 9, 1982

[54] PRESSURE SENSITIVE CLOSURE POUCH WITH INSERTABLE STERILIZATION INDICATOR

[75] Inventor: Arthur Hirsch, Elizabeth, N.J.

[73] Assignee: Arvey Corporation, Chicago, Ill.

[21] Appl. No.: 188,931

[22] Filed: Sep. 19, 1980

Related U.S. Application Data

[63] Continuation of Ser. No. 9,432, May 2, 1979, abandoned.

[51] Int. Cl.³ ............................................. B65D 79/00
[52] U.S. Cl. .................................. 206/439; 116/207; 116/216;. 116/DIG. 14; 116/DIG. 41; 229/62
[58] Field of Search ................ 206/439; 116/206, 207, 116/216, DIG. 14, DIG. 41; 229/62

[56] References Cited

U.S. PATENT DOCUMENTS

| | | | |
|---|---|---|---|
| 3,078,182 | 2/1963 | Crone, Jr. et al. | 116/207 |
| 3,311,084 | 3/1967 | Edenbaum | 116/207 |
| 3,372,861 | 3/1968 | Johnson et al. | 229/80 |
| 3,523,011 | 8/1970 | Bhiwandker et al. | 116/207 |
| 3,991,881 | 11/1976 | Augurt | 206/439 |
| 4,121,714 | 10/1978 | Daly et al. | 206/439 |

*Primary Examiner*—Stephen P. Garbe

*Attorney, Agent, or Firm*—Dressler, Goldsmith, Shore, Sutker & Milnamow, Ltd.

[57] ABSTRACT

A sterilizable pouch is provided with first and second opposing webs which are initially sealed together except for a region defining an open mouth. At least one of the webs has a strip of adhesive adjacent the mouth with a peelable release strip superposed upon and adhering to the adhesive strip for masking the adhesive strip from external contact before the pouch is closed and sealed. The peelable release strip includes an indicator means for indicating its exposure to a predetermined sterilization condition. The indicator means has an initial appearance signifying that the indicator means has not been subjected to the predetermined sterilization condition and is adapted to change to a final appearance after exposure to the predetermined sterilization condition for indicating such exposure. To use the pouch, an article is inserted within the pouch, the peelable release strip is removed from the adhesive and placed within the pouch next to the article, and the adhesive strip on one of the webs is brought into contact with the other web to close the mouth of the pouch. When the pouch is sterilized, the indicator means on the peelable release strip within the pouch changes appearance to indicate the attainment of the predetermined sterilization condition within the pouch.

2 Claims, 7 Drawing Figures

U.S. Patent    Nov. 9, 1982    Sheet 1 of 2    4,358,015
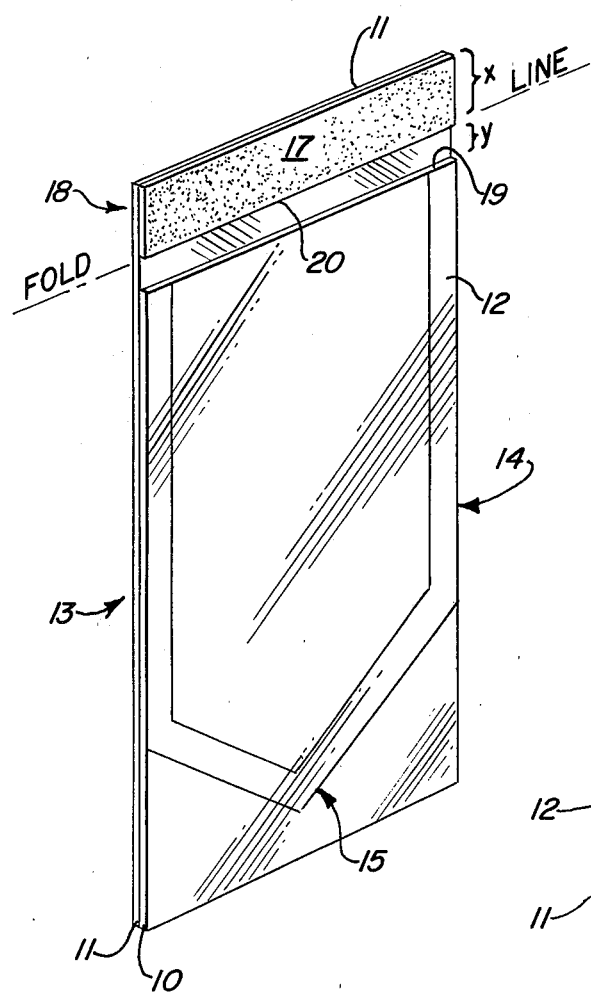
FIG. 1
PRIOR ART
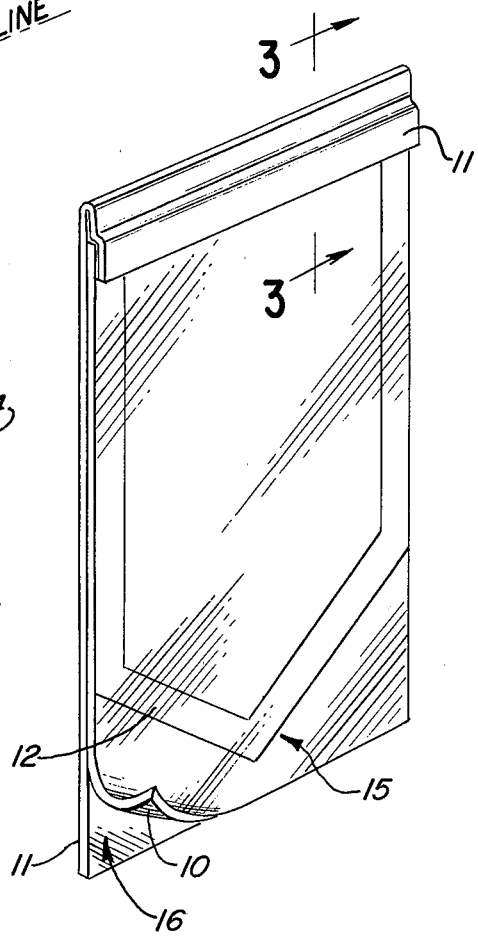
FIG. 2
PRIOR ART
FIG. 3
PRIOR ART

PRESSURE SENSITIVE CLOSURE POUCH WITH INSERTABLE STERILIZATION INDICATOR

DESCRIPTION

This application is a continuation of Ser. No. 009,432, filed May 2, 1979, now abandoned.

TECHNICAL FIELD

The present invention relates to sterilizable pouches used in medical facilities to sterilize patient care articles and instruments. More particularly, the present invention is directed to a pouch that is easy to use and has an integral indicator which can be placed inside of the pouch for indicating that a predetermined sterilization condition has been attained within the pouch.

BACKGROUND ART

Disposable pouches, including self-sealing pouches, are well known. Also known are sterilizable pouches which are permeable to the sterilizing medium such as steam or ethylene oxide. Usually, the pouch has two webs, one of which may be a transparent thermoplastic material to provide observation of the contents of the pouch and the other of which may be a paper or fiber material having a permeability suitable for use with the particular sterilizing medium employed.

In addition it is known in the medical field to provide pouches having an integrally formed indicator means, usually an impregnated chemical substance on the exterior surface of the pouch. The impregnated substance typically changes color after the pouch has been sterilized.

Indicating inks, such as chemically reactive inks, are also available for use as sterilization indicators. Such ink is available for use with ethylene oxide sterilization and the ink changes color on exposure to sterilization conditions. Typically, the exterior surface of some prior art pouches may be impregnated with such ink to form a sterilization indicator integral with the wall of the pouch.

Although the pouches that have an exterior surface sterilization indicator are available, many medical institutions choose not to rely on the exterior surface sterilization indicator as sole evidence that the inside of the pouch, and the article contained therein, has been properly sterilized. As a result, many medical institutions use one of a number of commercially available separate indicator devices, usually in the form of small strips of material, which can be inserted within the sterilizable pouch next to the article contained therein and which change appearance or color upon sterilization. This provides direct evidence that the interior of the pouch, and hence the article therein, has been properly sterilized.

Such commercially available indicator strips are typically impregnated with a material which is sensitive to, and usually chemically reacts with, the sterilizing medium, in such a manner so as to change appearance (e.g., color) when sufficient sterilization conditions have been achieved. For example, one such strip can be used with steam sterilization in autoclave units and includes a chemical-impregnated structure which turns to a different color when the minimum sterilization conditions of moisture, temperature and time have been achieved.

Though the separate indicator strips can provide adequate indication of the achievement of proper sterilization within the pouches, use of such strips has certain disadvantages. First, individual strips must be separately purchased. Second, adequate supplies of the strips must be maintained. Third, even if an adequate supply of indicator strips is available, the supply of strips must be provided at the location where the sterilizable pouches are used.

It would be desirable to provide a pouch having an indicator for signaling the achievement of sterilization conditions within the pouch and which avoids the shortcomings discussed above. Further, it would be desirable to provide a sterilizable pouch incorporating such an indicating strip in a structure which would be self-sealing to form a contaminant-proof seal.

SUMMARY OF THE INVENTION

In the preferred embodiment of the present invention, a sterilizable pouch is formed from first and second opposing webs which are sealed together except for a region defining an open mouth. The first web includes a flap extending outwardly beyond one edge of the second web in the mouth region.

A strip of adhesive is applied to one end of the first web adjacent to and spaced away from the edge of the second web at the mouth. Thus, there is defined on the first web an adhesive-free zone between the adhesive strip and the open mouth.

A fold line is defined at the edge of the adhesive strip closest to the open mouth and the adhesive strip has a sufficient width so that the flap can be folded about the fold line to seal the mouth with the adhesive strip adhering to both the adhesive-free zone on the first web and to an area of the second web to thereby form a contaminant-proof seal in the pouch.

Further, in accordance with the present invention, when the pouch is fabricated, a peelable release strip is superposed upon and adhered to the adhesive strip for masking the adhesive strip from external contact. The peelable release strip has an indicator means, such as indicating ink, for indicating the exposure of the strip to a predetermined sterilization condition (e.g., as by change of color of the indicating ink).

When the pouch is used for sterilization, an article is placed through the open mouth and into the pouch. Next, the peelable release strip is peeled away from the adhesive strip and inserted within the pouch next to the article therein. The pouch closure flap is then folded about the fold line to close and seal the mouth of the pouch. When the pouch is subjected to sterilizing conditions, the indicator on the peelable release strip changes from its initial appearance condition to the final appearance condition to indicate the attainment of a predetermined sterilization condition within the pouch.

The present invention is thus seen to provide an easy-to-use, self-sealing pouch with a contaminant-proof mouth seal in which the adhesive strip is initially protected by a peelable release strip and in which the peelable release strip also functions as a sterilization indicator within the pouch. There is no waste product produced during the initial placement of an article in the pouch and preparation of the pouch for sterilization. Thus, the present invention provides a pouch which requires only one waste disposal operation, that disposal operation arising only when the sterilized article is subsequently removed from the pouch at a later time.

Thus, it is seen that the combined effect of the various elements associated in accordance with the present invention is greater than the sum of the several effects of those elements taken separately. The novel combination of elements in accordance with the present invention yields desirable, beneficial and synergistic results—results which are not only new and different, but which also provide a substantial improvement over the prior art.

Numerous other advantages and features of the present invention will become readily apparent from the following detailed description of the invention and of one embodiment thereof, from the claims and from the accompanying drawings.

BRIEF DESCRIPTION OF THE DRAWINGS

In the accompanying drawings forming part of the specification, and in which like numerals are employed to designate like parts throughout the same, FIG. 1 is a front perspective view showing an unsealed prior art pouch;

FIG. 2 is a front perspective view of the prior art pouch of FIG. 1 in the sealed position;

FIG. 3 is an enlarged, fragmentary cross-sectional view of the embodiment of the sealed prior art pouch of FIG. 2 taken generally along the plane 3—3;

DETAILED DESCRIPTION OF THE PREFERRED EMBODIMENTS

Figure 4:
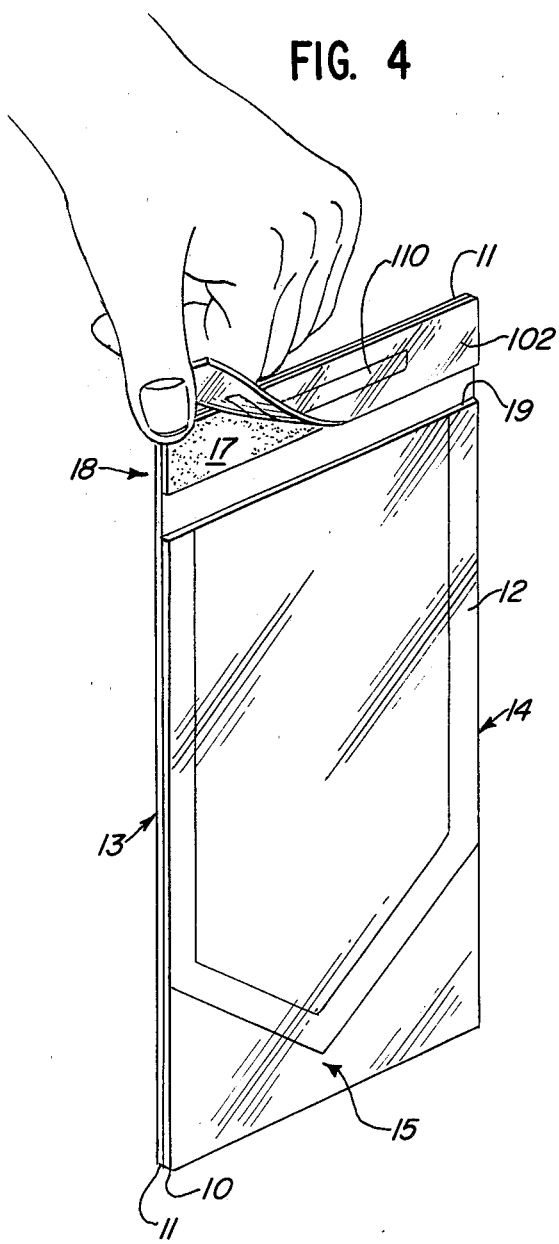
FIG. 4 is a pouch of the present invention in the unsealed condition showing a peelable release strip being removed therefrom.

While this invention is susceptible of embodiment in many different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components herein described are not essential to the invention unless otherwise indicated, since the invention is described with reference to an embodiment which is simple and straightforward.

Sterilizable pouches to which the present invention is particularly well suited are known in the prior art and one embodiment of such a prior art pouch is illustrated in FIGS. 1, 2, and 3. This prior art pouch is fully described in the above-referenced copending patent application Ser. No. 845,615 entitled, "Pressure Sensitive Tape Closure Pouch." In order to provide a basis for the understanding of the present invention, a brief description of this prior art pouch is presented here.

The pouch comprises two opposing webs 10 and 11. Web 10 is preferably a transparent thermally stable material such as coated or laminated polyethylene terephthalate sold under the trademark Mylar. Web 10 is sealed to opposing web 11 by heat seal 12. Web 11 is preferably made of a paper which is suitably permeable to the sterilizing media which is typically steam or ethylene oxide.

In a pouch of generally rectangular configuration the seal along respective pouch sides 13 and 14 is suitably a straight line along the side edges. Bottom seal portion 15 may be chevron-shaped leaving the webs unsealed in pouch area 16 to provide gripping means as is illustrated in FIG. 2. The chevron-shaped seal and gripping means cooperate to permit easy opening of the pouch.

Adhesive means 17, such as a double coated pressure sensitive transfer tape, may be applied across the surface of web 11 to a portion of flap area 18 as shown in FIG. 1.

The adhesive selected should be formulated from materials meeting Food and Drug Administration requirements for adhesives under FDA Section 121.2520. Suitably, the adhesive selected should give bonds that maintain contaminant-proof integrity from $-30°$ F. to $+350°$ F.

The adhesive on the pouch should also be selected to provide sufficient holding strength to the paper web to tear at least a portion of the web if the closure at the pressure sensitive seal is opened. In this manner a telltale is provided to give a clear warning that the pouch has been opened and the sterile seal has been broken. This will avoid accidental resealing of a sterilized pouch.

The bond strength of the adhesive should be minimally strong enough to cause fiber tear of the paper web whereby paper fibers visibly stick to the adhesive. It is also suitable for the pressure sensitive adhesive to bond with sufficient strength to the paper that the paper web is caused to tear when the pressure sensitive closure is opened.

Illustrative performance data for the pressure sensitive adhesive is a peel strength according to PSTC-3 of a 30 minute dwell 40 oz./in and a 24 hour dwell 50 oz./in. The adhesive has a shear strength of 165 hours pursuant to PSTC-7 for 1,000 gm at room temperature.

In the embodiment shown in FIG. 1 the adhesive is spaced a distance y from upper unsealed lip 19 of web 10. The distance y that the adhesive is spaced from lip 19 and the width x of the pressure sensitive adhesive are suitably related so that the width of the adhesive is broad enough to cover an area adjacent each side of lip 19 to form a continuous seal to prevent contamination of the contents of the pouch after sterilization. It has been found preferable to use an adhesive width x of about $\frac{3}{4}$ of an inch when the distance of space y is about $\frac{3}{8}$ of an inch. Thus, when the flap is closed the adhesive covers equal areas of $\frac{3}{8}$ of an inch on either side of lip 19. It should be appreciated that distance y that the adhesive is spaced from lip 19 may vary from about $\frac{3}{8}$ of an inch to $\frac{1}{2}$ inch or more. Similarly width x of the adhesive may also vary from about $\frac{3}{4}$ of an inch to one inch or more provided that the relationship of distance y and adhesive width x is sufficient to maintain a contaminant proof seal.

The embodiment of FIG. 2 shows the pouch illustrated in FIG. 1 in a closed position. The closure of FIG. 2 is obtained by folding flap 18 along the fold line generally defined by edge 20 the adhesive edge nearest lip 19. The flap is folded over to essentially seal paper web 11 to itself and to the area on web 10 as is best illustrated in FIG. 3.

Figure 5:
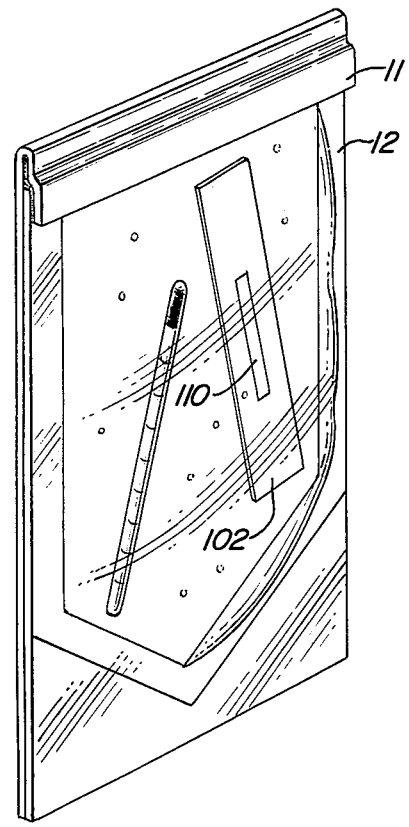
FIG. 5 is the pouch of the present invention illustrated in FIG. 4 in the sealed position and with the peelable release strip inserted within the pouch along with an article to be sterilized.

A first embodiment of the pouch of the present invention is illustrated in the unsealed configuration in FIG. 4 and in the sealed configuration in FIG. 5. In particular, with reference to FIG. 4, the pouch has a structure basically identical to that described above with respect to the prior art pouch illustrated in FIGS. 1, 2, and 3. However, in accordance with the present invention, a cover means, such as a peelable release strip 102 is superposed upon and adheres to the adhesive strip on web 11. The release strip 102 functions to mask the adhesive strip 17 from external contact before the pouch is filled with an article, closed, and sealed. As illustrated in FIG. 4, the release strip 102 is easily peeled away from the adhesive 17. To this end, the release strip 102 is made from a material, or is coated with a material, that is easily peeled away from the adhesive strip 17 without causing the adhesive strip 17 to be pulled away from the underlying web 11. Such peelable release strips and the materials for making such release strips are well known to those skilled in the art.

In accordance with the present invention, an indicator means, such as at impregnated region 110, is provided on the release strip 102, for indicating exposure to a predetermined sterilization condition. The impregnated region 110 may function as an indicator having an initial appearance condition (e.g., color or lack thereof) signifying that the indicator has not been subjected to a predetermined sterilization condition. The indicator is adapted to change to a final appearance condition (e.g., change in color) after exposure to a predetermined sterilization condition.

The indicator means or impregnated region 110 may have any particular shape and may, if desired, be formed into letters or words. In addition, the region 110 may be formed in or on either side of the peelable release strip 102 or may be impregnated entirely throughout the strip.

Preferably, the indicator means comprises an ink printed on the surface of the peelable release strip 102, which ink chemically reacts with the sterilizing medium and undergoes a change of color to indicate sterilization.

In use, the pouch of the present invention is supplied to a user with the peelable release strip 102 superposed upon and adhering to the adhesive 17. The user then inserts an article to be sterilized into the pouch and removes the release strip 102 as indicated in FIG. 4. The release strip 102 is placed inside the pouch along with the article to be sterilized and the flap 18 is folded over to seal the pouch. The sealed pouch, as illustrated in FIG. 5, is then sterilized. The change in the appearance of the indicator means or impregnated region 110 on the peelable release strip 102 is evidence that the interior of the pouch has been subjected to a predetermined sterilization condition.

It is seen that the present invention provides an improved economy which precludes the need to purchase separate indicating devices or indicator strips to be put inside sterilizable pouches. The invention also eliminates inventory and logistic problems since the indicator strip is part of the pouch and is thus available with the pouch whenever and wherever the pouch is used. Further, the combination indicator and peelable release strip protects the adhesive strip from contamination and accidentally sticking to other surfaces before the pouch is used. Additionally, initial removal of the peelable release strip 102 does not create any waste product since the release strip is inserted within the pouch. Thus, there is no need to provide for waste handling at the location where the pouches are filled and sterilized.

Figure 6:
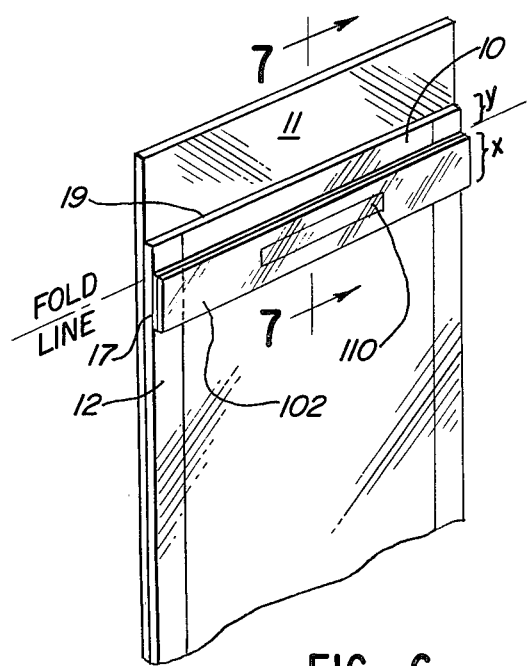
FIG. 6 is a front perspective view of another embodiment of an unsealed pouch of the present invention.
Figure 7:
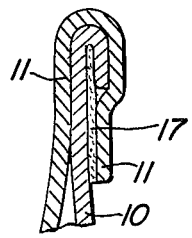
FIG. 7 is an enlarged, fragmentary cross-sectional view taken generally along the plane 7—7 in FIG. 6, but showing the pouch in the sealed position.

An alternate embodiment of the present invention is illustrated in FIGS. 6 and 7 which show the adhesive strip 17, having a width x, on the surface of web 10 rather than web 11. The release strip 102 covers the adhesive strip 17. As previously explained, the strip is spaced a distance y from lip 19. The distance y and the width x of the adhesive are cooperatively selected to provide a contaminant-proof seal. The closure of the embodiment illustrated in FIG. 6 is made by folding along a fold line generally defined by the edge of the adhesive nearest lip 19. As illustrated in FIG. 7, the closed pouch has the film of web 10 sealed to itself and to the flap of web 11 to form a contaminant-proof seal.

While the preferred embodiments of the present invention have been illustrated with reference to contaminant-proof seals, it is to be realized that the present invention may be incorporated with any type of peelable release strip which is superposed and adhering to an adhesive strip on a sterilizable pouch. Further, the present invention may be used on pouches made from many types of materials and in many different configurations.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

It is claimed:

1. In a sterilization pouch comprising first and second opposing webs which are sealed together except for a region defining an open mouth and comprising sealing means for closing the mouth of said pouch and including a strip of adhesive on at least one of said webs adjacent to said open mouth, the improvement comprising:

a peelable release strip superposed upon said adhesive strip, said release strip having an outer and an inner surface with said inner surface arranged in face-to-face contact with said adhesive strip and adhering thereto for masking said adhesive strip from external contact before said pouch is closed and sealed, said release strip including an indicator substance for indicating exposure to a predetermined sterilization condition, said indicator substance being present at least at said release strip inner surface and masked by an overlying thickness of said release strip and by said release strip outer surface, said indicator substance having an initial appearance color signifying that the indicator substance has not been subjected to said predetermined sterilization condition and said indicator substance further being adapted to change to a final appearance color upon exposure to said predetermined sterilization condition for indicating such exposure, said release strip being easily peelable from said adhesive strip whereby, when said release strip is removed from said adhesive strip and placed in said pouch and when said pouch is sealed and sterilized, said indicator substance changes from said initial appearance color to said final appearance color to indicate the attainment of said predetermined sterilization condition within said pouch.

2. The improvement in accordance with claim 1 in which said adhesive strip has a PSTC-3 peel strength of a 30-minute dwell 40 oz./in. and of a 24-hour dwell 50 oz./in. and in which said adhesive strip has a shear strength of 165 hours pursuant to PSTC-7 of 1,000 gm. at room temperature.

* * * * *